United States Patent
Strommer (10) Patent No.: US 7,792,243 B2
(45) Date of Patent: Sep. 7, 2010

(54) METHOD AND ARRANGEMENT FOR AUTOMATIC EXPOSURE CONTROL

(75) Inventor: Pekka Strommer, Espoo (FI)

(73) Assignee: Planmed Oy, Helsinki (FI)

( * ) Notice: Subject to any disclaimer, the term of this patent is extended or adjusted under 35 U.S.C. 154(b) by 166 days.

(21) Appl. No.: 12/066,758

(22) PCT Filed: Sep. 15, 2006

(86) PCT No.: PCT/FI2006/050390

§ 371 (c)(1),
(2), (4) Date: Mar. 13, 2008

(87) PCT Pub. No.: WO2007/034033

PCT Pub. Date: Mar. 29, 2007

(65) Prior Publication Data

US 2008/0226024 A1    Sep. 18, 2008

(30) Foreign Application Priority Data

Sep. 15, 2005    (FI) .................................. 20050921

(51) Int. Cl.
*A61B 6/04* (2006.01)
(52) U.S. Cl. ............................. 378/37; 378/97; 378/108
(58) Field of Classification Search ............. 378/37, 378/96, 97, 108–112
See application file for complete search history.

(56) References Cited

U.S. PATENT DOCUMENTS

| 5,365,562 | A | 11/1994 | Toker |
| 5,506,877 | A | 4/1996 | Niklason et al. |
| 5,751,783 | A | 5/1998 | Granfors et al. |
| 2002/0004630 | A1 | 1/2002 | Sarvazyan et al. |
| 2005/0169425 | A1 | 8/2005 | Takasawa |

FOREIGN PATENT DOCUMENTS

| WO | WO 98/21884 | 5/1998 |
| WO | WO 03/043497 | 5/2003 |
| WO | WO 2005/077277 | 8/2005 |

*Primary Examiner*—Courtney Thomas
(74) *Attorney, Agent, or Firm*—Cozen O'Connor (57) ABSTRACT

The invention relates to an automatic exposure control of an imaging implemented by electromagnetic radiation, in particular to prioritizing and selecting several automatic exposure signals in connection with mammography imaging, to be used in such a way that areas having darkened too little would not be left into the image to be formed, at least not in the area of the breast tissue. A selection process of the signals makes up an essential part of the invention, in which signals are selected for the basis of control of imaging parameters according to signal values, and possibly also according to the physical location of the signal sources, on the grounds of the selection criteria according to the invention.

30 Claims, 4 Drawing Sheets

METHOD AND ARRANGEMENT FOR AUTOMATIC EXPOSURE CONTROL

CROSS-REFERENCE TO RELATED APPLICATIONS

The present application is the U.S. National Phase of International Patent Application No. PCT/FI2006/050390, filed Sep. 15, 2006, which in turn is based upon and claims priority from Finnish Patent Application No. 20050921, filed Sep. 15, 2005, each of which is incorporated herein by reference in its entirety.

FIELD OF THE INVENTION

The present invention relates to automatic exposure control of an imaging being implemented by electromagnetic radiation, in particular to selecting signals to be used in automatic exposure control of mammography imaging in an arrangement where a number of signals are produced which are designed to be used for the automatic exposure control.

BACKGROUND OF THE INVENTION

In prior art, numerous different automatic exposure control (AEC) systems are known, which have been applied in connection with many different imaging solutions. In diagnostic X-ray imaging, exposure automation plays a very important role because its incorrect operation may lead to over- or underexposure and, consequently, to an unnecessary increase in the radiation dose received by the patient and to uncertain or even false diagnoses due to poor image quality. Failed exposures can of course be corrected by re-imagings, but they further increase the radiation dose received by the patient and, on the other hand, also cause extra work.

The operation of the automatic exposure systems of the film-based apparatuses currently in use is typically based on empiric methods, in which a huge number of test exposures are done for new film/intensifying screen combinations using different imaging values of the imaging apparatus and varying the thickness, generally in range of 20-80 mm, of the acrylic plate typically used to represent the object to be imaged. Depending on the details of operation of the automatic exposure system used in each case, its various parameters are adjusted according to the results obtained until a sufficiently constant degree of film darkening is achieved in all circumstances. Each time when a new film/intensifying screen combination appears on the market or when more demanding tolerance requirements are set, such measurement series have to be carried out anew.

In the solutions according to the prior art in which electric imaging technology is applied, the automatic exposure control is typically realized by using a slightly different principle, because a dynamic range of an imaging detector is notably wider than that of a film and over-exposure of some areas of the object is not a problem in these solutions, because one will be able to get those areas visible anyway later by means of image processing. The principles of tuning of the automatic exposure system is nevertheless the same as in the film based technology, i.e. bundles of acrylic plates are exposed and such imaging parameters are looked for, empirically, by which the level of the signal being created at the detector remains substantially the same.

The commonly used tuning method as described above is thus based on imaging of a homogeneous plate, generally made of acrylic, simulating the object to be imaged. The periodic inspections carried out by the authorities to test the exposure automatics are based on the same method, which in respect of repeatability of the test is, evidently, necessary. However, in an actual imaging situation, the object being imaged is not necessarily homogeneous. For example, the breast tissue imaged in mammography is by no means homogeneous, nor is the breast of standard size or shape in its overall dimensions. While in mammography the object is typically also imaged from different projections, its shape and position in the imaging area may vary for this reason, too.

For the purpose of reducing problems of automatic exposure systems being based on a single detector signal only, approaches that make use of several AEC signals have been developed. In some of them, signals of those detectors have been arranged to be automatically disregarded in which the amount of radiation received exceeds some preset level. Such a limit level may be set such that, in order to reach it, it is obvious that the detector is located completely or partially outside the tissue being imaged. Solutions have also been developed, in which that one out of the few detectors is selected, whose signal appears to be the most suitable. While these solutions have significantly reduced exposure errors, they still don't necessarily guarantee that also the lightest regions of the image being formed in the imaging will become dark enough.

In particular in mammography, there are special problems of its own being caused by not only the abovementioned non-homogeneity of the breast tissue in regard to attenuation of the radiation used for the imaging as such, but also by the possibility of imaging, in addition to the breast tissue, a silicon implant or muscular tissue of the armpit area, for example. Further, in some imaging modes, even parts of the apparatus used for the imaging may get included in the image. When a cancer tumor often locates just within the densest places of the breast tissue, it would be essential to get especially those places imaged adequately black. One is not necessarily able to achieve this, though, in case the exposure control is based, for its essential part or completely even, on such a signal which corresponds a region which attenuates the radiation even more than the densest place of the breast tissue (in regard to the attenuation of radiation used for the imaging). Such an outcome may occur in the case if one decides to elect the lowest signal to be the abovementioned most suitable signal, for example, but this very signal in question happens to be measuring radiation having penetrated e.g. a silicone implant.

SUMMARY OF THE INVENTION

The object of this invention is, thus, to reach a new kind of way to elect, out of the signals produced by the sources of exposure signals, the ones to be used for exposure control in such a way that in the image being formed, even the lightest places representing the breast tissue itself will become imaged black enough. As far as imaging in electric form is concerned, this means in practice that an adequate signal level will be reached (in practice, adequate SNR signal-to-noise ratio or CNR=contrast-to-noise ratio) even at the places of the imaging detector producing the lowest signal.

One preferable embodiment of the invention utilizes a method in which, of the tissue type of the tissue to be imaged at a time, regional deviations from the average are found out and, for the use of the exposure automatics, those signals are elected which correspond the area/the areas of the breast tissue itself which absorbs/absorb radiation used for the imaging the most.

BRIEF DESCRIPTION OF THE DRAWINGS

Objects of the invention are achieved by the invention as defined in more detail in the accompanying claims, which invention will be described in more detail in the following with the help of some of its preferable embodiments and by referring to the attached figures, of which figures.

DETAILED DESCRIPTION OF THE INVENTION

Figure 1:
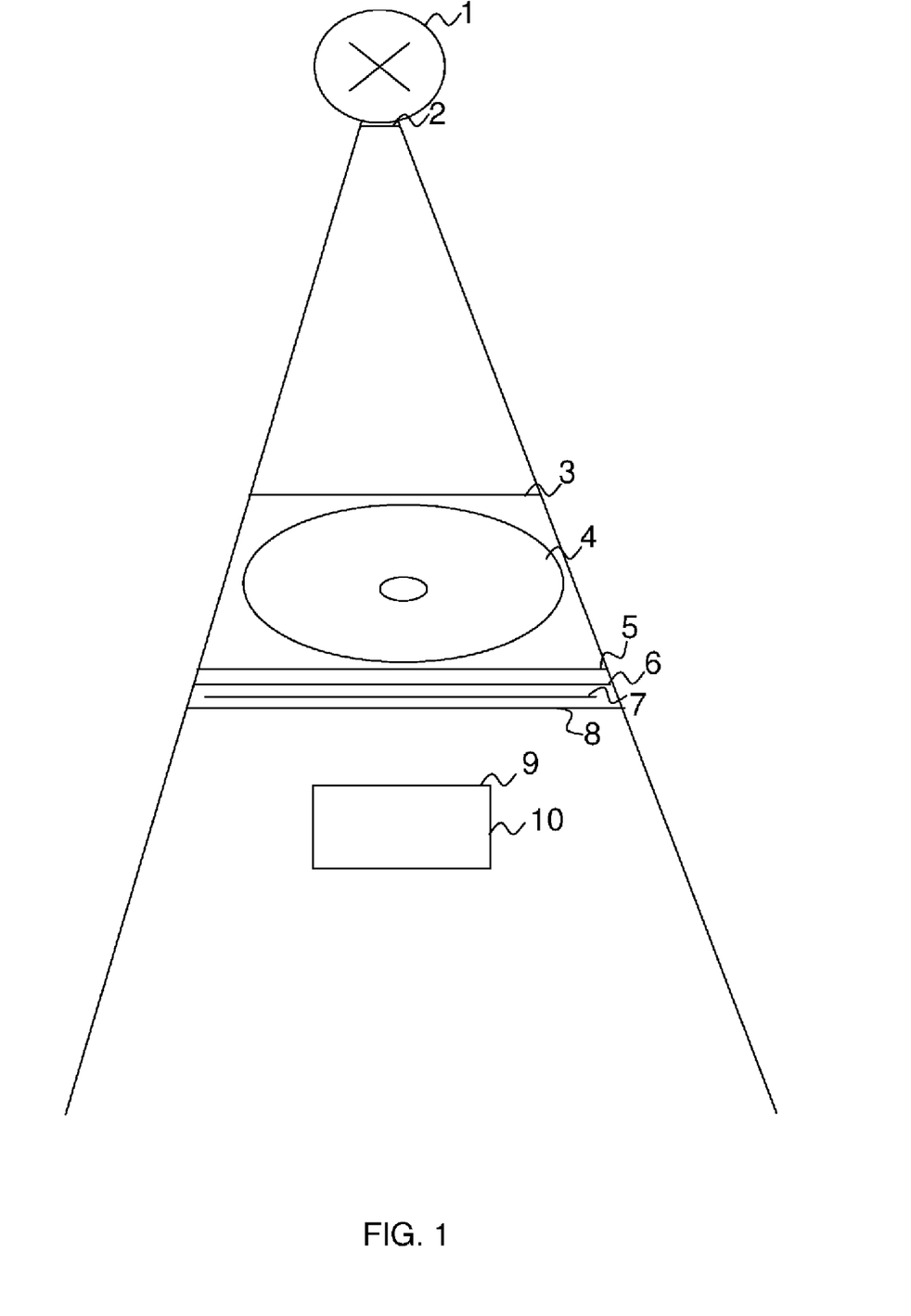
FIG. 1 presents a cross-sectional view of structures of a typical film-based mammography apparatus, which remain in the area of the radiation beam during imaging.

In FIG. 1 there is presented, as a cross-sectional view, structures of a typical film-based mammography apparatus, which are penetrated by an x-ray beam produced by an x-ray tube (1) during imaging. According to FIG. 1, such structures include a filter (2), an upper compression plate (3) compressing the breast in the imaging area, a breast (4), a lower compression plate (5), a cover of a film cassette (6), a film (7), a bottom of a film cassette together with an intensifying screen (8) and a cover (9) of an AEC detector (10).

Within an embodiment of the invention, to be represented in more detail below, materials and thicknesses, in the direction of the beam, of all of these components of the construction may be stored in a memory of an imaging apparatus, or of a computer connectable to it, along with information about different filters to be used in the apparatus, about different films intended to be used in film cassettes and about their intensifying screens, about thickness of an epitaxial layer of the exposure detector and so on, needed in the calculation processes of the exposure automatics in question. Based on empirical tests, a table of radiation produced by the X-ray tube at some of its operating parameter values is stored in the memory. In solutions implementing electric imaging in which, typically, the imaging detector itself is used as the source of the exposure signal, the magnitude being measured in the exposure automation is actually the same as the magnitude to be controlled (the image signal), such a modeling thus being slightly simpler when relation of the magnitude to be controlled to the amount of photons/quanta received by the film needs not to be separately established.

Figure 2:
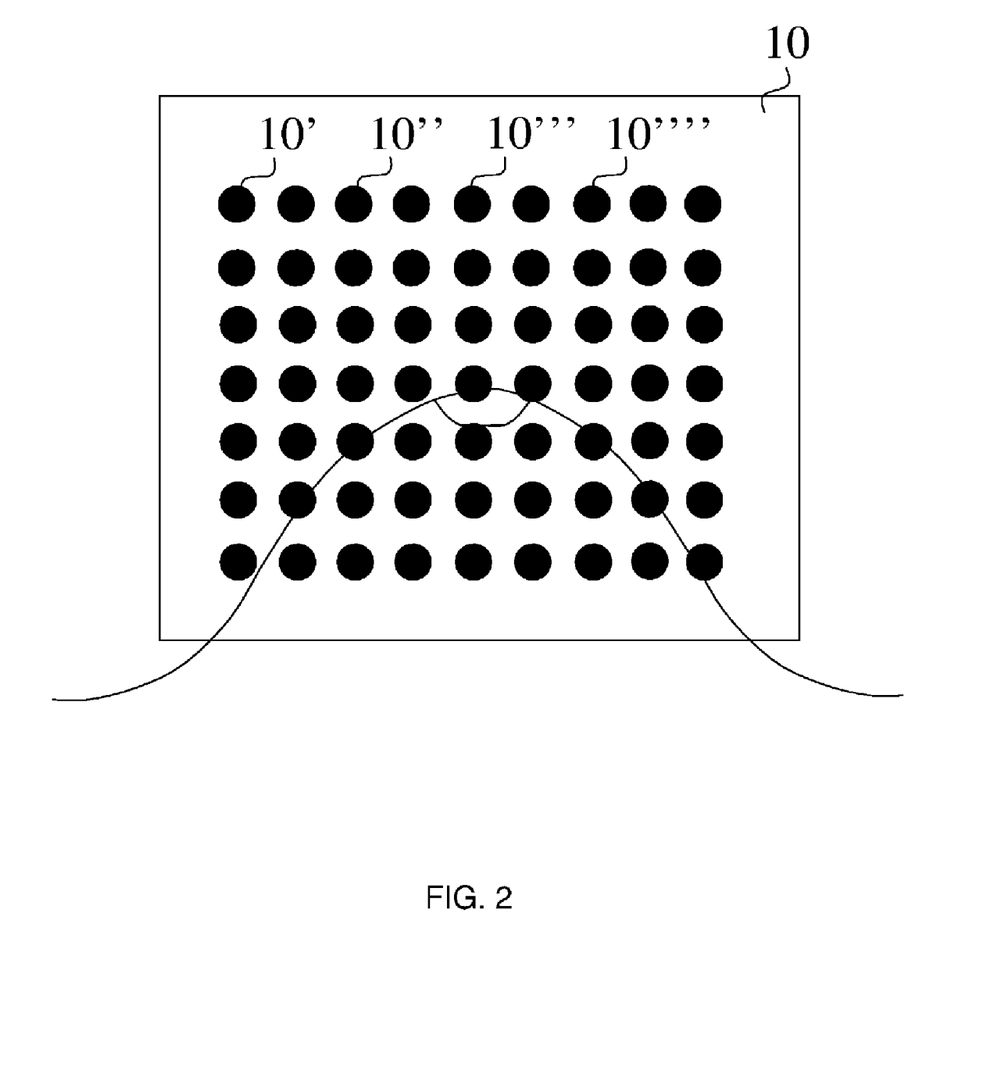
FIG. 2 presents an exposure detector construction applicable for use in connection with an embodiment of the invention, consisting of several small detectors.

FIG. 2 ja presents an arrangement known as such, in which automatic exposure signals are measured at several different locations at small local areas. By current technology, it is no more an actual cost issue to arrange in the AEC detector (10), for example, several dozens of small detectors (10', 10", . . . ) even, as spread scattered within the area of the object, in which case it is possible to get a representative view, by means known as such, of the matter of how great a portion of the tissue (4) is of average density and/or deviates from it in either direction, and weight the exposure control accordingly. The signals possibly being left completely or partly outside the object being imaged, i.e. detectors which are completely or partly exposed to direct radiation, may be left to have a small weight or totally ignored. By such a solution, one is able to get at least such a situation under a satisfactory control, too, in which the object contains areas of such widely varying densities that there is no possibility to achieve a result that is optimal in all respects, in other words, in which the required dynamic range would be too broad. In such a case, the imaging parameters may be optimized so that a result is achievable in which a maximal portion of the tissue being imaged is still readable from the image. In electric imaging, instead of separate AEC detectors, one may use signals readable at individual pixels or groups of pixels of the imaging detector. One may thus interpret FIG. 2 showing also an electric full-field detector (10), for example, in which a number of pixels or groups of pixels (10', 10", . . . ) are arranged to be used for producing AEC signals.

According to the present invention, an automatic exposure method is realized by positioning the object to be imaged within the imaging area, after which radiation used for imaging is produced by the radiation source, radiation containing image information is detected by means for receiving image information and radiation having passed through the object is measured at several locations, and out of signals so attained at least a portion is selected to be utilized for controlling one or several imaging parameters in connection with the imaging such that signals to be utilized for controlling said one or several imaging parameters are selected in a selection process, in which signals are selected either a desired number in the order of magnitude by beginning from the lowest signal, or alternatively signals are selected in order as many as possible by beginning from the lowest signal in such a way that the remainder between the mean value of the selected signals and said lowest signal is lower than a desired limit value. In this selection process, either at least two signals are selected, or so many that weight of the possible signal values not representing breast tissue remains low, such as selecting that many signals, for example, that weight of signals being lower than a predetermined selection criterion remains lower than desired or, alternatively, prior to beginning of the selection process, such signals which fulfill a predetermined exclusion criterion are left out of the selection process.

Building up the abovementioned selection criterion may be based on signal values, which would presumably correspond, or do computationally correspond signal values of radiation passed through something else than breast tissue, such as radiation having passed through muscular tissue, silicone implant or some element of the imaging apparatus. Depending on the case, weight of the possible low signals not representing tissue desired to become imaged can be get so small that a satisfactory end result may be reached, after all, even by using an adequately large number of signal sources, such as of the order of ten or twenty, and by selecting for the basis of control an adequately large number of signals, such as at least five or at least ten. Like this, then, according to one preferable embodiment of the invention, one is able to determine such a desired minimum criterion for the signal that signals lower than that will not be selected to be included in the selection process at all.

Essentially, the signals selected in the selection process are used as computationally weighted in a desired manner, for controlling at least one imaging parameter in such a way that at least such an amount of radiation would penetrate at least such an area of the object to be imaged, which area the signal calculated from the signals selected in the selection would correspond, that the area in question would be imaged at least as dark as desired. Preferably, and especially when such signals are first left outside of the actual selection process according to a desired disregarding criterion, whose values are so low that they probably correspond signal values of some something else than radiation having passed through breast tissue, a mean value of the selected signals is calculated, which mean value is used as an automatic exposure signal according to the invention for controlling the value of at least one imaging parameter, such as exposure time.

Figure 3:
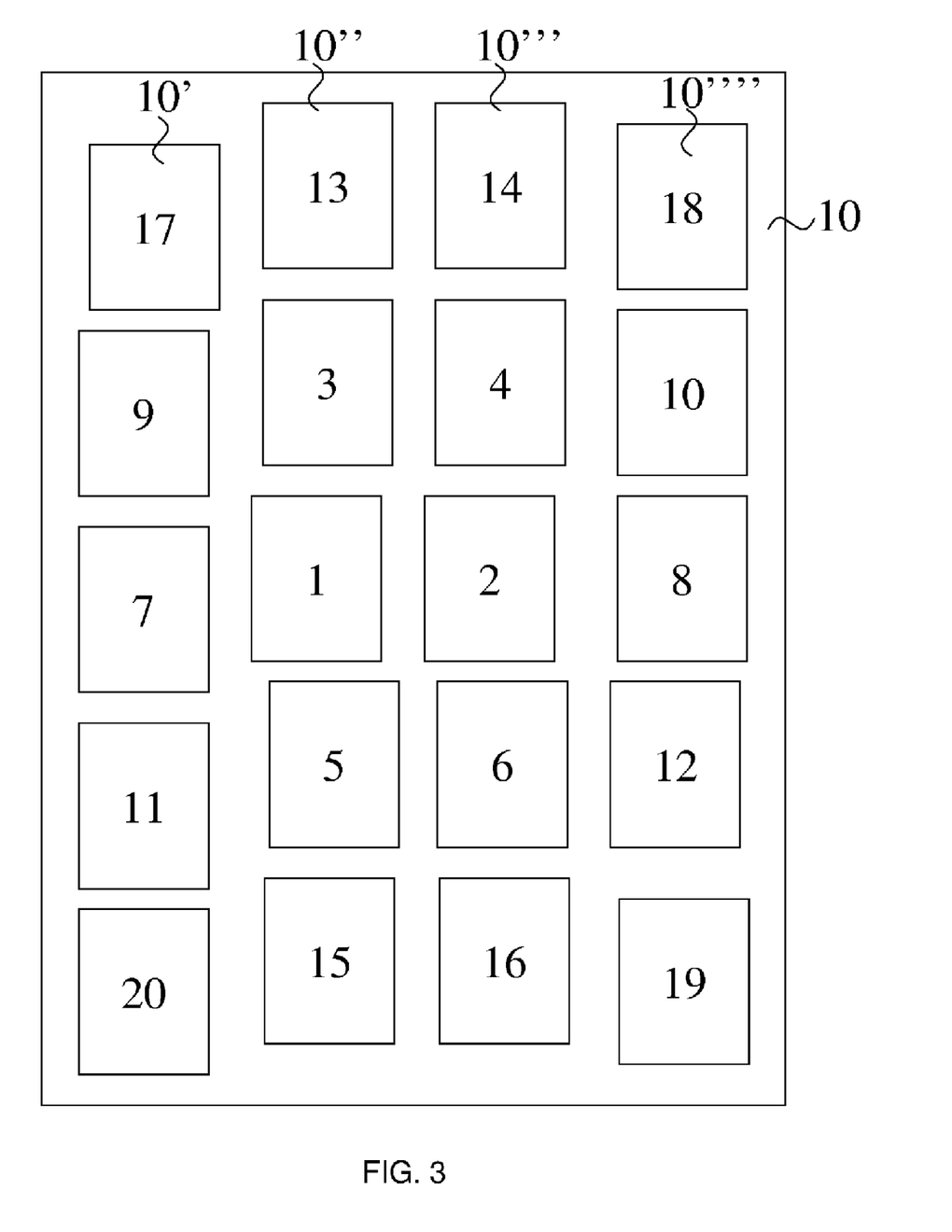
FIG. 3 presents a possible manner according to a preferable embodiment of the invention for arranging the signal sources according to their physical location.

According to the invention, the signals selected to the selection process may also be first divided according to their order of magnitude into desired value ranges characteristic to various tissue types. In such a case, the selection process may be realized by first selecting signals from the value range including the lowest signal values, then signals from the next lowest value range and so on in such a way that within each value range, signals are selected according to the order of physical location criterion of the signal sources producing them. One possible such an order of location criterion is presented in FIG. 3. When following this kind of secondary selection criterion being based on physical location of the signal source, one may select primarily those signals out of the signals of the same order of magnitude, which presumably represent the most relevant area of the object being imaged, from the point of view of desired kind of behavior of the automatic exposure function. Thus, in case the desired limit criterion is fulfilled, i.e. selection of signals ends after selection of the first signal of such a signal value region, for example, in which one out of two signal sources has physically located in the area of breast tissue and the other in the area of armpit, particularly that signal will be included into the automatic exposure which has been received from the area of breast tissue. This physical location criterion can be arranged to prioritize the area of the breast tissue, for example, which lies at a distance from the tip of the breast, concerning smaller breasts essentially the middle section of the area becoming imaged, concerning the bigger breasts otherwise correspondingly, but an area lying relatively closer to the tip of the breast.

When it was stated earlier that those signals being lower than/corresponding a desired selection criterion can accordingly to the invention be directly left outside of the actual signal selection process, correspondingly, also signals belonging to a particular region or particular regions of signal values, i.e. in fact signals corresponding to a particular tissue type or particular tissue types, can be directly left out of the actual signal selection process. Such a range of values being left out of the selection process may include not only low signals but also signals that are higher than a desired criterion. Essentially, particularly when determining/using criteria based on tissue type, thickness of the object to be imaged in the direction of radiation, when being positioned in the imaging area, is taken into account. Then, one may proceed e.g. such that one gives a value 100% to signal value/thickness combinations corresponding in practice the most dense breast tissue possible, a value 99% to a tissue type that absorbs radiation slightly less etc. and use these parameters in the signal selection method according to the invention. In such a case, limit value of the selection criterion could be 100%, for example, and the exclusion criterion could include parameter values >100%. Naturally, there are other ways to determine these kinds of criteria and their limit values, too, and e.g. determining the limit value needs not to be based on absolutely (presumably) specifically the most dense breast tissue possible.

In the invention, one is thus able to use as signal sources e.g. individual pixels or pixel groups of detectors of an electric receiver of image information, or automatic exposure detectors arranged behind the receiver of image information, such as a film.

Figure 4A:
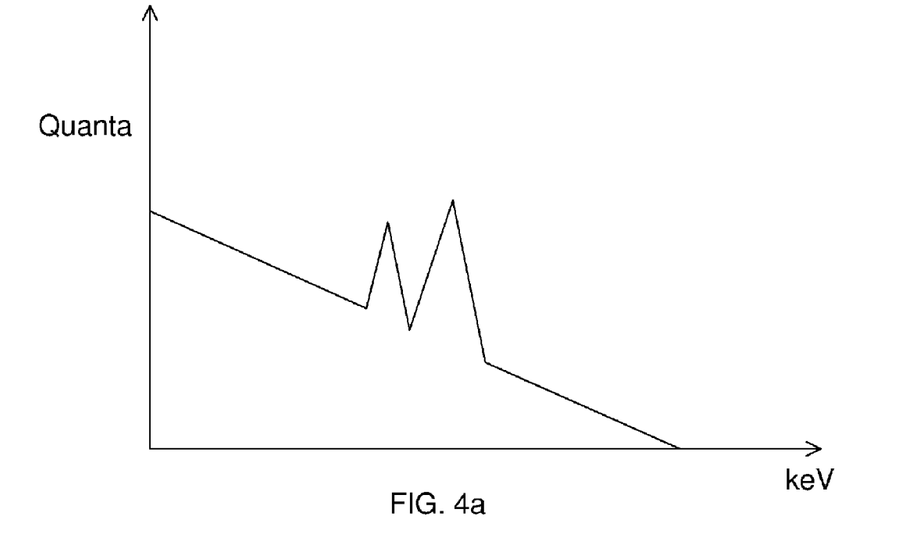
FIGS. 4a and 4b present typical spectra of radiation received from an x-ray tube before and after filtration.
Figure 4B:
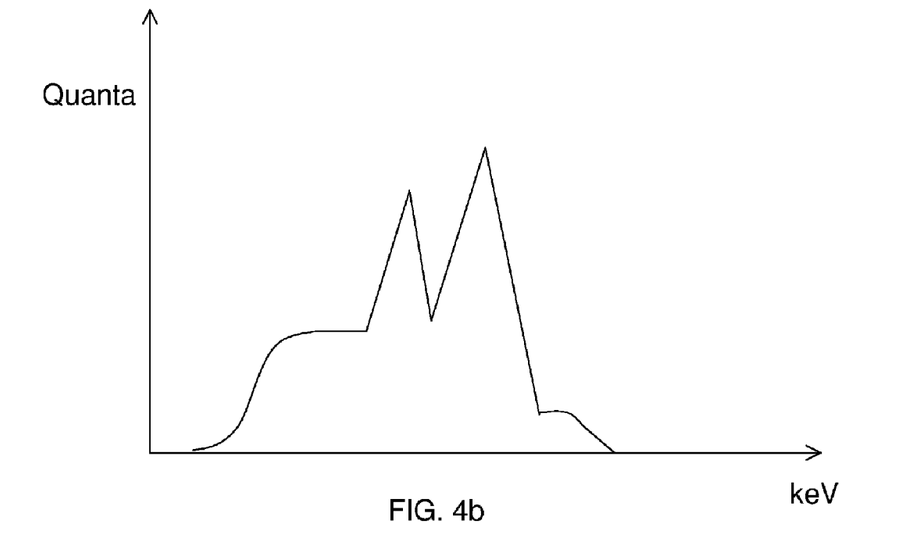

So, an automatic exposure signal produced according to the invention can preferably be utilized in a method and arrangement in which control of at least one imaging parameter is based on information, modeled in advance, of attenuation of radiation spectrum while it travels from a radiation source (1) of a mammography apparatus to a receiver of image information (7). In such a solution, one may proceed e.g. in such a way that upon initiation of the imaging process, first, kV and mA used in the imaging are fed to the x-ray apparatus or, alternatively, the control system of the apparatus may also select by itself the values it presumes optimal based on the distance between compression plates (3, 5) after the breast has been compressed between them to its imaging position. Now, based on the data stored in the memory, one gets to know precisely already at this stage, in advance, i.e. already prior to initiation of the exposure, the spectrum of radiation leaving the x-ray tube (1). Further, when one has knowledge of the material being used to filter the radiation leaving the x-ray tube (1) and its thickness and further, the corresponding data of the compression plate, one is able to precisely determine by calculation the spectrum of radiation entering the breast (4) being imaged. In FIGS. 4a and 4b has been presented by way of an example, how the spectrum attained by some operating values of the x-ray tube (1) and materials may change after having passed though a filter (2) (FIG. 4b).

When the compression thickness of the breast (4), which is the object being imaged, is known, it is possible to computationally establish even before the exposure is started what would the radiation spectrum having penetrated it be with the imaging parameters used, if the tissue was of average nature and thus, further, to determine what the radiation spectrum falling on each AEC detector (10', 10", . . . ) used in the apparatus would be, in this case as in the embodiment as illustrated in FIG. 1, after the radiation has further passed through the lower compression plate (5), the film cassette and its intensifying screen (6, 7, 8) and the cover (9) of the AEC detector, the properties of which are known. Thus, on the basis of this computed spectrum, and e.g. the thickness of the epitaxial layer of the diodes typically used as AEC detectors, it is also possible to calculate by means known as such what the electric signal generated at each of the detectors should then be.

The actual AEC function is started after a short period from the beginning of imaging, whereupon on the basis of the signal received from the AEC detector and the known imaging parameters and tissue thickness data, on is able to find out which kind of the tissue density the measured AEC signal corresponds, after which it is further possible to calculate the effect of the tissue, whose density is now known, on the radiation spectrum having passed through the tissue. So, finally, in the case of film application, for example, one is able to accurately determine how the film darkens at each location per signal units measured by the exposure detectors and adjust the imaging parameters, especially exposure time, to the optimal.

In this way, consequently, according to a preferable embodiment of the invention, at least part of the components lying between the radiation source and means for receiving image data, and further possible other components used in the method possibly remaining in front of the exposure detectors, are modeled with respect to attenuation of radiation, the thickness of the object to be imaged in the direction of radiation, when positioned for imaging, is determined, exposure is initiated, signals received at the exposure signal sources are measured and used for determining which density with respect to the modeled attenuation these signals correspond to, after which signals are selected according to the selection process of the invention, the mean value or some other, weighted value is calculated from the selected signals and based on said modelings and said calculated signal value and the tissue thickness in question, such changes possibly needed in the operating parameter values used in the exposure, especially in the exposure time, are determined such that the area of the object corresponding to the computational signal in question would darken in a desired amount at least, and values of the imaging parameters are adjusted accordingly.

Further, it is possible according to the invention to determine the signals, which one should receive from the exposure signal sources taking into account the radiation spectrum used for the imaging, the thickness of the tissue and the attenuation of radiation according to said modelings presuming that attenuation in the object to be imaged is typical and average to the breast tissue, determine the exposure time corresponding to the signal according to said modelings in question, initiate exposure, measure the signals received at said signal sources, select signals according to said selection process and calculate the mean value or some other, computationally weighted value of said selected signals, compare said computational value with corresponding exposure signal value determined based on modelings, and in case said computational value deviates from said predetermined value more than a preset limit criterion, adjust exposure time, and/or some other imaging parameter such that at least the tissue region corresponding to said computational signal value would darken at least in a desired amount by using the parameter values in question.

Further, one may utilize the signal values measured, said modeling, information of the thickness of the object and possibly information of the location of the signal sources, for determining those signal sources which appear to be measuring specifically radiation having passed breast tissue and based on these signals weight the exposure control, secondarily and within the limits of what is possible, also such that no part of the image to be formed will darken too much.

The modelings of changes of the spectrum presented above can be made with the help of equation describing attenuation of coherent monochromatic radiation known as such, taking into account the material and thickness of the element to be modeled. As far as film application is concerned, it is preferable to model also the speed of darkening of the image detected on the film as a function of radiation received by it, whereat said values of the imaging parameters can be adjusted to correspond values needed to achieve the desired darkening by taking into account in the modeling both the x-ray quanta directly absorbed to the film after having passed through the cover of the film cassette and, based on modeled spectrum of radiation having passed through the cover of the film cassette, the photons having been converted at the intensifying screen of the film cassette and emitted to the film therefrom. Preferably, such a film is used whose deviation of darkening from the law of reciprocity is known and the exposure time adjusted accordingly, i.e. by taking into account the modeled exposure time leading to the desired darkening according to the correction coefficient characteristic to the film type used.

Without departing from the basic concept of the invention, many other items of information based on or calculated from empirical tests as well as other pieces of information and calculation models can be stored in memory, to be utilized in the exposure automatics. Such information may include e.g. control algorithms, known as such, for adjustment of other imaging parameters besides exposure time to be utilized e.g. when the imaging parameter values believed to be optimal in the starting situation turn out to be, on the basis of the measured AEC signal, significantly different from the values which would enable an optimal imaging result to be achieved as a function of e.g. exposure time, kV, mA, focus size of the X-ray tube etc. used, and as a function of possible different combinations of these.

One may identify those signal sources from the exposure automation signals, which apparently lie completely or partly outside the breast tissue being imaged based on the measurement result produced by them being much too high, i.e. because the breast typically does not contain tissue having such a low density. Likewise, on the basis of suitable criteria built into the system, signal sources lying very close to the edge of the tissue being imaged can be identified and partly or completely taken off from the selection process according to the invention. Signal of at least one detector possibly lying outside of the object can be used for measuring e.g. radiation output of the radiation source and thus for compensating possible variations in the production of radiation.

According to the invention, an automatic exposure control system may be realized, to be implemented in a mammography apparatus, which includes means for positioning the object (3, 5) to the imaging area, radiation source (1) for producing radiation to be used for imaging, means for detecting (7) the radiation including image information, means for creating a control signal and for controlling at least one imaging parameter based on said control signal. Then according to the invention the arrangement includes signal sources, which are arranged to measure radiation having passed through the object at several locations and the control signal in question is arranged to be created from at least part of the signals so attained. The arrangement also includes means for storing data, in which a programme routine including procedures relating to automatic exposure for selecting those signals, which are used for creating the control signal in question, is stored. Those procedures in question, relating to automatic exposure the programme routine may include, have already been described above and are thus not repeated here anew.

In the foregoing described invention and its embodiments are not limited to the solutions described above; instead, they may vary within the scope of the following claims.

The invention claimed is:

1. Method for automatic exposure control of a mammography apparatus, in which radiation to be used in the imaging is produced at the radiation source, in which radiation including image information is detected by a means for receiving image information and in which radiation having passed through the object being imaged is measured at several locations and in which out of the signals thus attained, at least a portion is selected to be utilized for controlling one or more values of imaging parameters in connection with the imaging, wherein the signals to be utilized for controlling said one or more values of the imaging parameters are selected in a selection process in which signals are selected, either, a desired number in the order of their values beginning from the lowest signal value or, alternatively, as many signals as possible are selected by starting from the lowest signal value such that the difference between a mean value of the selected signals and said lowest signal value is smaller than a desired limit value, wherein said selection process includes
   i) selecting either at least two signals or selecting a number of signals so that weight of those possible lowest value signals not representing breast tissue remains low, or
   ii) prior to initiating the selection process, leaving outside the selection process such possible signals which fulfill a predetermined exclusion criterion.

2. Method according to claim 1, wherein in connection with said selection process, first, the signals are divided according to their order of magnitude into signal groups of different respective value ranges representing different respective tissue types, whereupon in the selection process one selects first signals from the value range including lowest value signals, then signals from the next lowest value range etc. so that within each signal group, signals are selected according to a desired physical location criterion of the signal sources producing the signals.

3. Method according to claim 2, wherein said physical location criterion of the signal sources is arranged to prioritize an area of breast tissue which locates at a distance from the tip of the breast, wherein said area to be prioritized in the case of smaller breasts is essentially the middle section of the area being imaged, and wherein said area to be prioritized in the case of bigger breasts corresponds to that in the case of smaller breasts except that said area to be prioritized lies relatively closer to the tip of the breast.

4. Method according to claim 1, wherein said exclusion criterion for the signals is defined to include a criterion, according to which those signals are left out of said signal selection process whose signal values are so low as to approximate signal values of radiation having passed through something other than breast tissue, and such signals are left out of said signal selection process.

5. Method according to claim 1, wherein said signals are measured by signal sources, and wherein individual pixels or pixel groups of an electric detector of image information or automatic exposure detectors arranged behind the receiver of image information are used as said signal sources.

6. Method according to claim 1, wherein signals selected in said selection process are used as weighted in a desired manner for controlling at least one imaging parameter value such that at least such an amount of radiation would penetrate at least such an area of the object to be imaged, which area the signal calculated from the signals selected in the selection process would correspond, that the area in question would become imaged at least as dark as desired.

7. Method according to claim 6, wherein a mean value is calculated from the values of the selected signals.

8. Method according to claim 2, wherein when determining said value range, tissue type and/or selection/exclusion criteria, and when comparing signal values with the respective criterion, information of the thickness of the object being imaged, in the direction of the beam when the object is positioned in the imaging area, is used.

9. Method according to claim 1, wherein the method includes prior to said selection process,
modeling the radiation spectrum obtained from the radiation source of the imaging apparatus as a function of at least the essential operating parameters and production of radiation quanta,
modeling at least some of the components of the imaging apparatus that lie between the radiation source and the image data receiving means, and further of the possible other components used in the method that possibly lie in front of the exposure detectors, with respect of attenuation of radiation,
determining the thickness of the object to be imaged, in the direction of the beam when the object is positioned within the imaging area, and
initiating the exposure, measuring the signals attained from the exposure detectors, and determining the density of the object being imaged in relation to the modeled attenuation of radiation these signals correspond to, after which,
signals are selected according to said selection process, a mean value or some other, weighted value of the selected signals is calculated and based on said modelings and said calculated signal value and the tissue thickness in question, those changes in the operating parameter values used in the exposure, especially in the exposure time, are determined that would be needed so that the area of the object corresponding to the computational signal in question would darken to a desired degree at least, and values of the imaging parameters are adjusted accordingly.

10. Method according to claim 9, wherein said changes in the spectrum are modeled by using an equation describing attenuation of coherent monochromatic radiation, taking into account the material and thickness of the element being modeled.

11. Method according to claim 9, wherein a film is used as a means for receiving image data and wherein darkening speed of the image on the film used as means for receiving image data is modeled as a function of radiation received by it and values of said imaging parameters are adjusted to correspond to values required to reach the desired darkening, in which modeling of darkening of the film both the x-ray quanta directly absorbed by the film after having passed through a cover of the film cassette and, based on modeled spectrum of radiation having passed through the cover of the film cassette, the photons having been converted at the intensifying screen of the film cassette and emitted to the film therefrom.

12. Method according to claim 9, wherein the signals are determined, which one should receive from the exposure signal sources when attenuation of radiation is typical and average for the breast tissue taking into account the radiation spectrum used for the imaging, the thickness of the tissue and the attenuation of radiation according to said modelings, the exposure time corresponding to the signal according to said modelings in question is determined, exposure is initiated, the signals received at said signal sources are measured, signals according to said selection process are selected and a mean value, or some other, computationally weighted value of values of said selected signals is calculated, said computational value is compared with a corresponding exposure signal value determined based on modelings, and in case said computational value deviates from said predetermined value more than a preset limit criterion, the exposure time, and/or some other imaging parameter is adjusted such that at least the tissue region corresponding to said computational signal value would darken at least in a desired degree when using the parameter values in question.

13. Method according to claim 1, wherein those signals are completely or at least partly left out of the selection process which are so high that, taking into account the order of magnitude of the density of the object being imaged, their signal sources cannot be located in the area of radiation which has passed through the object being imaged.

14. Method according to claim 9, wherein those signal sources are determined, which seem to be measuring specifically radiation having passed through breast tissue by utilizing the measured signal values, said modeling, information of thickness of the object and possibly information of location of the signal sources and, within the limits what is possible, exposure control is secondarily weighted based on these signals such that no portion of the image being formed darkens too much.

15. Method according to claim 1, wherein said selection process includes selecting a number of signals so that the weight of those possible lowest signals not representing breast tissue remains low, which selecting is implemented by selecting a number of signals so that the weight of the signal values which are lower than a predetermined limit criterion remains lower than desired.

16. Arrangement for automatic exposure control to be used in a mammography apparatus, which mammography apparatus includes means for positioning the object (3, 5) in an imaging area, a radiation source (1) producing radiation used for imaging, means for detecting (7) radiation including image information, means for creating a control signal and for controlling at least one imaging parameter during imaging based on said control signal, which arrangement includes signal sources, which have been arranged to measure radiation having passed through the object being imaged at several locations and said control signal is arranged to be created from at least part of the signals such attained, wherein the arrangement includes means for storing information, in which a program routine for selecting those signals which are used for creating said control signal has been stored, said means comprising the following functions:

signals are selected in a selection process either in a desired amount in the order of their values beginning from the lowest signal value or, alternatively, as many signals as possible are selected by starting from the lowest signal value such that the difference between a mean value of the selected signals and said lowest signal value is smaller than a desired limit value, wherein said selection process includes, i) selecting at least two signals or selecting a number of signals so that the weight of those possible lowest value signals not representing breast tissue remains low, or ii) prior to initiating the selection process, leaving such possible signals out of the selection process which fulfill a predetermined exclusion criterion.

17. Arrangement according to claim 16, wherein said program routine includes a function according to which said selection process includes steps of, first, dividing the signals according to their order of magnitude into signal groups of different respective value ranges representing different respective tissue types, whereupon in the selection process one selects first signals from the value range including lowest signals, then signals from the next lowest value range etc so that within each signal group, signals are selected according to the desired physical location criterion of the signal sources producing them.

18. Arrangement according to claim 17, wherein in said programmed routine, physical location criterion of the signal sources is arranged to prioritize an area of breast tissue which locates at a distance from the tip of the breast, wherein said area in the case of smaller breasts is essentially the middle section of the area being imaged, and wherein said area to be prioritized in the case of bigger breasts corresponds to that in the case of smaller breasts except that said area to be prioritized lies relatively closer to the tip of the breast.

19. Arrangement according to claim 16, wherein said programmed routine includes a function, according to which such signals are left out of said selection process, whose signal values are so low as to approximate signal values of radiation having passed through something other than breast tissue, when they are compared with at least one predetermined exclusion criterion for the signals.

20. Arrangement according to claim 16, wherein in the arrangement, individual pixels or pixel groups of an electric detector of image information, or automatic exposure detectors arranged behind the receiver of image information, are used as said signal sources.

21. Arrangement according to claim 16, wherein said programmed routine includes a function, according to which signals selected in said selection process are used as weighted in a desired manner for controlling at least one imaging parameter value such that at least such an amount of radiation would penetrate at least such an area of the object to be imaged, which area the signal calculated from the signals selected in the selection process would correspond, that the area in question would become imaged at least as dark as desired.

22. Arrangement according to claim 21, wherein said programmed routine includes a function, according to which a mean value of the selected signals is calculated from the values of the selected signals.

23. Arrangement according to claim 17, wherein said program routine includes a function, according to which when determining said value range, tissue type and/or selection/exclusion criteria and when comparing signal values with the respective criterion, information of the thickness of the object being imaged, in the direction of the beam when the object is positioned in the imaging area, is used.

24. Arrangement according to claim 17, wherein the radiation spectrum obtained from the radiation source of the imaging apparatus is modeled in the arrangement as a function of at least the essential operating parameters and production of radiation quanta, and with respect of attenuation of radiation at least some of the components of the imaging apparatus that lie between the radiation source and the image data receiving means, and further of the possible other components used in the method that possibly lie in front of the exposure detectors, wherein the arrangement includes means for determining thickness of the object to be imaged, in the direction of the beam and when the object is positioned within the imaging area, wherein said programmed routine performs a function, according to which after initiation of the exposure the signals attained from the exposure detectors are measured, and the density of the object being imagined, in relation to the modeled attenuation of radiation these signals correspond to, is determined, after which signals are selected according to said selection process, a mean value of the values of the selected signals or some other, weighted value of the selected signals is calculated and based on said modelings and said calculated signal value and the tissue thickness in question, those changes in the operating parameter values used in the exposure, especially in the exposure time, are determined that would be needed so that the area of the object corresponding to the computational signal in question would darken to a desired degree at least, and values of the imaging parameters are adjusted accordingly.

25. Arrangement according to claim 24, wherein changes of spectrum are modeled in the arrangement with the help of equation describing attenuation of coherent monochromatic radiation, by taking into account the material and thickness of the modeled element.

26. Arrangement according to claim 24, wherein a film is used as a means for receiving image data and wherein darkening speed of the image on the film used as means for receiving image data is modeled in the arrangement as a function of radiation received by it and values of said imaging parameters are adjusted to correspond to values required to reach the desired darkening, in which modeling of darkening of the film both the x-ray quanta directly absorbed by the film after having passed through the cover of a film cassette and, based on modeled spectrum of radiation having passed through the cover of the film cassette, the photons having been converted at the intensifying screen of the film cassette and emitted to the film therefrom.

27. Arrangement according to claim 24, wherein said programmed routine includes a function, according to which the signals are determined which one should receive from the exposure signal sources when attenuation of radiation is typical and average for the breast tissue taking into account the radiation spectrum used for the imaging, the thickness of the tissue and the attenuation of radiation according to said modelings, the exposure time corresponding to the signal according to said modelings in question is determined, exposure is initiated, the signals received at said signal sources are measured, signals according to said selection process are selected and a mean value or some other, computationally weighted value of the values of said selected signals is calculated, said computational value is compared with a corresponding exposure signal value determined based on modelings, and in case said computational value deviates from said predetermined value more than a preset limit criterion, the exposure time, and/or some other imaging parameter is adjusted such that at least the tissue region corresponding to said computational signal value would darken at least in a desired degree when using the parameter values in question.

28. Arrangement according to claim 16, wherein said programmed routine includes a function, according to which those signals are completely or at least partly left out of the selection process which are so high that, taking into account the order of magnitude of the density of the object being imaged, their signal sources cannot be located in the area of radiation which has passed through the object being imaged.

29. Arrangement according to claim 24, wherein said programmed routine includes a function, according to which those signal sources are determined, which seem to be measuring specifically radiation having passed through breast tissue by utilizing the measured signal values, said modeling, information of thickness of the object and possibly information of location of the signal sources and, within the limits what is possible, exposure control is secondarily weighted based on these signals, such that no portion of the image being formed darkens too much.

30. Arrangement according to claim 16, wherein said selection of a number of signals so that the weight of those possible lowest signals not representing breast tissue remains low is implemented by selecting a number of signals so that the weight of the signal values which are lower than a predetermined limit criterion remains lower than desired.

* * * * *